United States Patent [19]

Meathrel

[11] Patent Number: 4,597,942
[45] Date of Patent: Jul. 1, 1986

[54] DEVICE TO INDICATE THE CONCENTRATION OF ETHYLENE OXIDE IN THE WORKPLACE

[75] Inventor: William G. Meathrel, Gananoque, Canada

[73] Assignee: Graphic Controls Canada Ltd., Ganonoque, Canada

[21] Appl. No.: 523,050

[22] Filed: Aug. 15, 1983

Related U.S. Application Data

[63] Continuation-in-part of Ser. No. 497,807, May 25, 1983.

[51] Int. Cl.⁴ .................................... G01N 21/78
[52] U.S. Cl. ................................. 422/57; 422/87; 436/1; 436/93
[58] Field of Search .......................... 73/23; 116/206; 422/55–58, 86–88, 119; 436/1, 93, 142, 165, 167, 169, 902

[56] References Cited

U.S. PATENT DOCUMENTS

| | | | |
|---|---|---|---|
| 2,998,306 | 8/1961 | Huyck et al. | 422/56 |
| 3,258,312 | 6/1966 | Olson | 436/93 |
| 3,409,404 | 11/1968 | Fergason | 436/125 |
| 3,992,154 | 11/1976 | Whitbourne et al. | 436/93 |
| 4,015,937 | 4/1977 | Miyamoto et al. | 436/93 |
| 4,160,008 | 7/1979 | Fenocketti et al. | 436/165 |
| 4,327,575 | 5/1982 | Locker | 422/88 |

Primary Examiner—Arnold Turk
Attorney, Agent, or Firm—Michael G. Berkman

[57] ABSTRACT

A visual indicator device and dosimeter in which a liquid crystal composition deposited on an opaque dark-colored carrier substrate undergoes color changes which depend on the concentration, and total quantity, of ethylene oxide to which the device has been exposed. The device serves both to monitor the concentration of ethylene oxide in the environment and to indicate a time-weighted average exposure.

11 Claims, 5 Drawing Figures

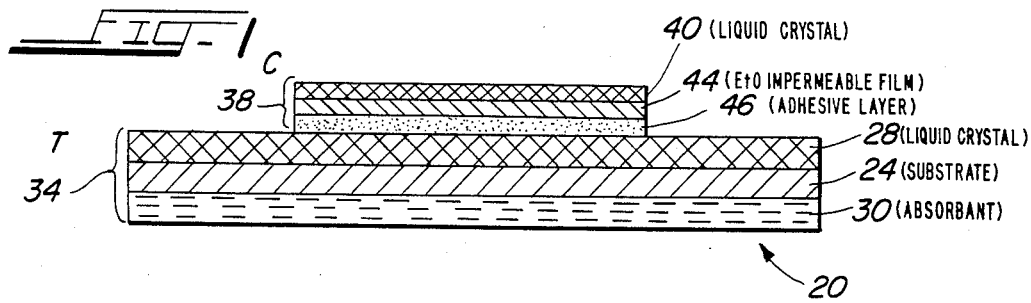
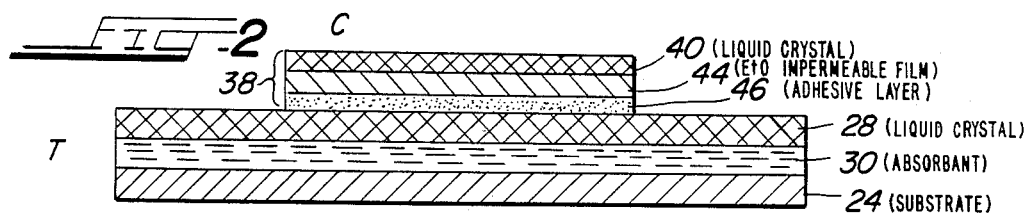
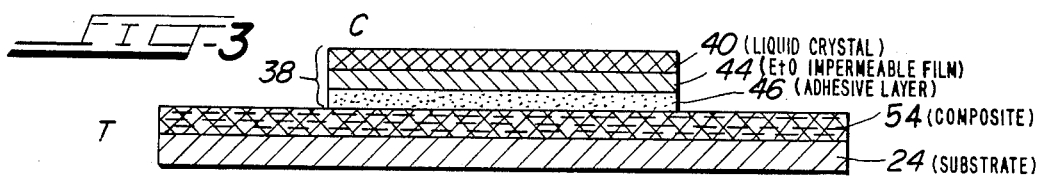
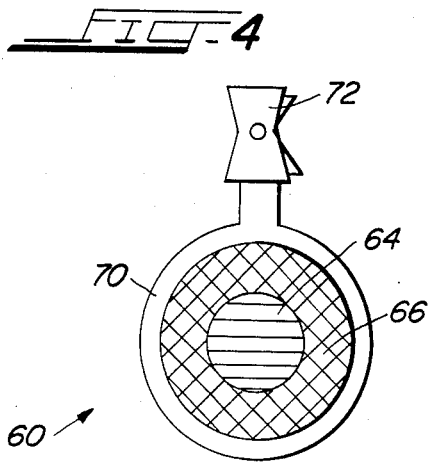
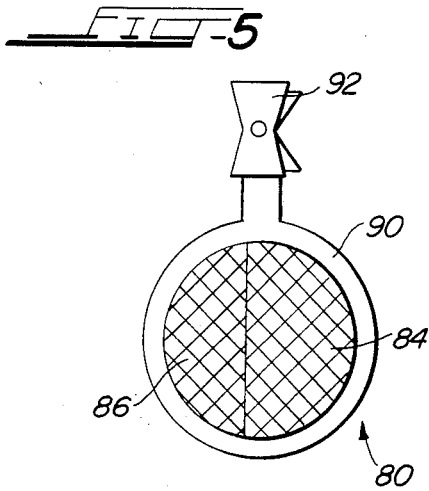

DEVICE TO INDICATE THE CONCENTRATION OF ETHYLENE OXIDE IN THE WORKPLACE

BACKGROUND OF THE INVENTION

The present invention is a Continuation-in-Part of applicant's prior application Ser. No. 497,807, filed May 25, 1983, and the entire disclosure of that application is hereby specifically incorporated herein by reference, to the extent it is not inconsistent herewith.

Ethylene oxide is produced extensively in the United States to produce ethylene glycol used in antifreeze and to produce chemical products such as surfactants. Ethylene oxide is also used in industry and in health care facility to sterilize heat-sensitive materials. It is used as a fungicide for treatment for fumigation and also as a foodstuffs sterilant. The effects upon the human body are not yet fully known, but there is a consensus that exposure to ethylene oxide is dangerous and should be minimized. (J. W. Yager, C. J. Hines, R. C. Spear, *Science*, Vol. 219, p. 1221, Mar. 11, 1983); (C. Hogsteclt, N. Malmquist, B. Wadman, *JAMA*, Vol. 241 (1), p. 1132, March, 1979). There has been widespread recognition of the mutagenetic potential of ethylene oxide, and recent evidence has led to a National Institute for Occupational Safety and Health (NIOSH) recommendation to treat ethylene oxide as a suspect carcinogen and to use appropriate control measures. The U.S. Department of Labor's Occupational Safety and Health Administration has proposed a 1 ppm Time-Weighted Average (TWA) Permissible Exposure Limit (PEL) (*Federal Register*, Vol. 48 #78, p. 17284, Rule 29CFR part 1910, Apr. 21, 1983). Adequate monitoring of ethylene oxide in the workplace environment is essential for employee health and safety.

Currently, there are a number of devices available for environmental monitoring of ethylene oxide. These devices include a pneumatic composition transmitter (PCT) which is an analog gas chromatograph developed by the Foxboro Company (Foxboro, Mass.) A Foxboro/Wilks MIRAN infrared Analyzer can also be used to measure ethylene oxide in the environment. Ethylene oxide has a characteristic infrared spectrum, and measurement at one wavelength such as 11.8 $\mu$m provides a quantitative measure of ethylene oxide concentration. Ametallic oxide semiconductor monitor such as the Gas Tech monitor (Gas Tech Inc., Mountain View, CA) can be used to monitor ethylene oxide levels in the environment. for ethylene oxide.

In addition to continuous monitoring, short term or grab-sampling measurements of ethylene oxide in the environment are used. National Draeger has a number of gas and vapor detection and measurement grab-sampling tubes including one which measures ethylene oxide in the environment.

Of particular interest are devices for personal monitoring of worker exposure to toxic vapors, especially ethylene oxide. There are several categories of personal monitors. One active type of personal monitor consists of a small battery-powered pump that can be worn by an employee. Air is drawn at a pre-set rate, and airborne contaminants are absorbed into a collecting device positioned near the employee's breathing zone. The collecting device may contain an absorbant such as activated charcoal. Collected contaminants are thermally desorbed and analyzed using gas chromatography techniques. Alternatively, the collecting device may be a sampling bag such as a Tedlar TM (DuPont) bag. The collected air is analyzed using normal analytical procedures.

Passive type monitors such as 3M's Ethylene Oxide Monitor (U.S. Pat. Nos. 3,950,980; 3,924,219; 4,102,201) and DuPont's Pro-tek Ethylene Oxide Monitoring Badge have been used by attaching near the breathing zone where airborne contaminants are absorbed. After exposure, these monitoring devices are resealed, then returned to the manufacturer for analysis. These environmental monitoring devices and procedures are described in the *Federal Register* (Vol. 48 #78, p. 17284, 1983).

General information on liquid crystals and their properties is available in many publications. For example: "Molecular Structure and the Properties of Liquid Crystals" by G. W. Gray, published by Academic Press; "Liquid Crystals-Citations from the NTIS Data Base", published by the U.S. Department of Commerce, June 1980; and "Liquid Crystals—A colorful State of Matter" by G. H. Brown and P. P. Crooker in *Chemical and Engineering News*, pp. 24–37, Jan. 31, 1983.

The use of liquid crystals as vapor detectors has been reported in the above references and in others. Fergason, U.S. Pat. No. 3,409,404, teaches the use of cholesteric liquid crystals for the quantitative and qualitative analysis of matter, particularly gas. E. J. Poziomek, T. J. Novak, and R. A. Mackay in their paper entitled "Use of Liquid Crystals as Vapor Detectors", Mol. Cryst. Liq. Cryst., Vol. 27, pp. 175–185, 1973, describe the effect of organic vapors on liquid crystal films positioned between crossed polarizers. Neary, U.S. Pat. No. 4,285,697 describes a food spoilage indicator comprising liquid crystal cholesteric compositions which exhibit color change when exposed to gases formed during food decomposition. W. R. Lawton, U.S. patent applicatron Ser. No. 241,226, now U.S. Pat. No. 4,495,291, teaches the use of cholesteric liquid crystals to determine when the amount of residual ethylene oxide in sterilized items has reached a safe level. Lawton's invention is based on the differential in color of a cholesteric liquid crystal coating in a control and test area. The test area is a portion of the liquid crystal coating sealed beneath a transparent cover sheet, preferably plasticized polyvinyl chloride. When there is a difference in color between the control and test areas, then the concentration of ethylene oxide remaining in the permeable cover sheet exceeds the response concentration of the liquid crystal coating.

SUMMARY OF THE INVENTION

The instant specification describes a personal monitor which is affixed near the breathing zone. Airborne contaminants interact with a liquid crystal coating which exhibits a color change dependent on the concentration of the contaminant. This device gives an immediate visual indication of the exposure to a contaminant. Specifically, the present invention is directed to a device which gives an immediate indication of the time-weighted average exposure as well as the peak exposure to ethylene oxide. By simple modification of the liquid crystal coating, the devices of the invention may be used to monitor other vapors or gases e.g. nitrous oxide, in the environment.

The indicator device described herein uses a liquid crystal coating whose color is dependent on the ethylene oxide concentration in the environment. In addition, by combining the liquid crystal coating with an absorbant material which absorbs ethylene oxide from the environment, the indicator device when worn near the breathing zone can be used to indicate personal exposure to ethylene oxide over a time-weighted average.

Cholesteric liquid crystal formulations which exhibit a color change when exposed to ethylene oxide are used in the indicator device. Since these liquid crystal formulations may also exhibit a color change due to temperature variations, it is necessary to compensate for temperature effects on the indicator response. The difference in color between a control area which responds to temperature and a test area which responds to both temperature and ethylene oxide can be used as a quantitative measurement of the exposure level of ethylene oxide.

The aims, objects and features of the invention will be better understood upon reference to the drawings which illustrate, schematically, preferred structures for an ethylene oxide dosimeter according to the invention.

BRIEF DESCRIPTION OF THE DRAWINGS

FIG. 1 is an enlarged cross-sectional schematic representation of one preferred embodiment of a multi-layer liquid crystal containing dosimeter, according to the invention;

FIG. 2 is a second embodiment of the dosimeter of the invention;

FIG. 3 is another embodiment of the invention;

FIG. 4 is a schematic representation of one form of a badge incorporating the features of the present invention; and FIG. 5 is a second embodiment of a badge utilizing the teachings of the invention.

DESCRIPTION OF PREFERRED EMBODIMENTS

The aims and objects of the invention are achieved, in accordance with the invention, by providing a person-borne badge-like indicator device which contains, in addition to a film of a gas sensitive liquid crystal composition, an absorbant for retaining and accumulating ethylene oxide present in an ambient environment. In a preferred embodiment the invention constitutes a dosimeter in which there is automatic temperature-effect compensation effected through use of a test zone and a control zone.

Referring now to the drawings, and more particularly to FIGS. 1 through 3, there are shown, for purposes of disclosure, preferred embodiments of devices invoking the principles and incorporating features of the invention. Each embodiment includes a test area T and a control area C.

In FIG. 1 the sensor and indicator device 20 is seen as including a porous or permeable substrate or support sheet 24 for a first liquid crystal coating 28. This support sheet 24 is preferably black or made black by coating with a substance such as black paint. A preferred substrate medium is 3 mil black paper.

On the underside of the substrate 24 is a layer of absorbant 30 which absorbs ethylene oxide from the environment. Typical absorbants include silica gel G/HR (J. T. Baker Chemical Co.), Alumina Absorption (Fisher Scientific Company), and activated charcoal such as Columbia JXC Activated Charcoal (Union Carbide). The absorbant layer 30 may be bonded to the substrate 24 using aqueous or organic resin solutions such as an aqueous 5% solution of gelatin or a toluene solution of Acryloid B44 (Rohm and Haas). Rather than used as a film-like coating the absorbant 30 may be compressed into a pellet which is bonded to or mounted against the substrate 24.

The liquid crystal coating 28 is preferably applied to the substrate 24 in a medium which binds the liquid crystal composition to the substrate 24. Microencapsulated liquid crystals may also be used and coated on the substrate using gelatin or polyvinyl alcohol aqueous solutions, aqueous cellulose-type polymers solutions containing Hercules' Natrosol or Klucel resins, or latex type resins such as Reichhold's DL3261. Non-encapsulated liquid crystal coating formulations can be prepared using solutions of the cholesteric esters in organic solvents and various resins. Acrylic resins such as Rohm and Haas Acryloid resins are preferred. The preferred ratio of cholesteric esters to resin solid are those which prevent the liquid crystal coating from being 'greasy'. Normally, one part liquid crystal formulation to 3–4 parts resin solids are used in the liquid crystal coating. Various organic solvents may be used; however, they must not adversely affect the substrate or the cholesteric esters. Preferred solvents include toluene, ethanol, acetonitrile, xylene, methylethyl ketone, and cellosolve.

The liquid crystal coating formulation is prepared by melting the cholesteric esters, then combining the melted esters with a suitable binder and liquid solvent. Alternatively, the cholesteric liquid crystals can be microencapsulated according to known encapsulation procedures (Churchill et al., U.S. Pat. No. 3,697,197). The microencapsulated liquid crystals can be applied directly to the substrate 24, although preferably the microencapsulated liquid crystals would be combined with an aqueous based binder such as a 5% aqueous solution of gelatin prior to applying to the substrate 24.

The cholesteric liquid crystal composition used in the sensor is one which exhibits a color change when exposed to ethylene oxide. It is preferred to employ a mixture of three or four different types of cholesteric liquid crystals. The mixture preferably includes 30% to 80% by weight of a cholesteryl ester of a fatty acid having from 6 to 20 carbon atoms, from 5% to 40% of a member selected from the group consisting of cholesteryl oleyl carbonate and cholesteryl (2-alkoxyethoxy) ethyl carbonates where the alkoxy group has 1 to 4 carbon atoms, and from 0.5% to 30% of a member selected from the group cholesteryl benzoate, cholesteryl p-nitro benzoate, cholesteryl cinnamate, cholesteryl cinnamyl carbonate, cholesteryl phenylazo phenol carbonate, cholesteryl chloride, and cholesteryl bromide, or mixtures thereof.

Some preferred formulations are given in the Examples listed below in which the concentrations are given in parts by weight.

| EXAMPLE I | |
|---|---|
| Cholesteryl nonanoate | 57.59 |
| Cholesteryl benzoate | 14.22 |
| Cholesteryl oleyl carbonate | 23.43 |
| Cholesteryl 2-(2-ethoxyethoxy) ethyl carbonate | 4.76 |
| EXAMPLE II | |
| Cholesteryl nonanoate | 54.47 |
| Cholesteryl benzoate | 14.93 |
| Cholesteryl oleyl carbonate | 24.60 |
| Cholesteryl 2-(2-ethoxyethoxy) ethylcarbonate | 5.00 |
| Cholesteryl phenylazophenol | |

|   |   |
|---|---|
| carbonate | 1.00 |
| EXAMPLE III | |
| Cholesteryl nonanoate | 61.30 |
| Cholesteryl cinnamyl carbonate | 21.10 |
| Cholesteryl benzoate | 17.60 |
| EXAMPLE IV | |
| Cholesteryl nonanoate | 60.30 |
| Cholesteryl cinnamyl carbonate | 21.10 |
| Cholesteryl benzoate | 16.80 |
| Cholesteryl phenylazophenol carbonate | 1.00 |

In FIG. 1, structures 30, 24, and 28 form the test area 34 of the indicator. The absorbant layer 30 extracts and concentrates ethylene oxide from the environment while the liquid crystal coating 28 responds to the ethylene oxide in the absorbant 30. The absorbant 30 may include an attenuating agent to regulate diffusion of gas from the ambient system into the liquid crystal coating 28. Alternatively, the attenuator may constitute a separate layer of material.

A second layered system defines the control area 38 of the indicator 20 of the invention. The control area 38 includes a liquid crystal coating 40 applied to an ethylene oxide impermeable barrier film 44 which is in turn bonded through an adhesive layer 46 to an upper surface 50 of the liquid crystal layer 28. An adhesive tape such as Fasson Med 3044 is suitable for use as the adhesive layer, and the ethylene oxide impermeable barrier 44 is preferably a black solid material such as a metallic disc, the latter being coated with the same liquid crystal coating formulation as used in the test area.

In the absence of ethylene oxide, both liquid crystal layers 28 and 40 exhibit the same color. That color depends both on the liquid crystal coating composition and the ambient temperature. When placed in an environment containing ethylene oxide, both liquid crystal coatings 28 and 40 will undergo perceptible color changes if the concentration of ethylene oxide exceeds the sensitivity of the liquid crystal composition. The degree of color change correlates with a peak exposure to ethylene oxide. If the concentration of ethylene oxide in the environment does not exceed the sensitivity of the liquid crystal coating formulation, the color of structures 28 and 40 will remain unchanged. Then ethylene oxide is extracted from the environment by the absorbant 30. The liquid crystal coating 28 will exhibit a color change when the concentration of ethylene oxide extracted by the absorbant 30 exceeds the threshold sensitivity of the liquid crystal coating composition 28. Since both the control 40 and test surface 28 are at the same temperature, any temperature effect will be "cancelled" and the difference in color between these areas will provide an immediate indication of the quantitative ethylene oxide exposure concentration.

The present aim of the invention is to provide a sensor which is capable of indicating exposure to ethylene oxide over an eight-hour period. There are difficulties in utilizing a visual color comparison to determine ethylene oxide exposure at these very low concentrations. In order to increase the sensitivity of the indicator to the limit of 1 ppm over eight hours or to other levels set by official agencies, an instrument such as a colorimeter or a color comparator may be used to determine a color difference between the control 38 and test areas 34. In addition, rather than using a color comparison between the control and test areas as a quantitative indication of ethylene oxide exposure, other properties of the liquid crystal coating may be relied upon for the quantitative measurement of ethylene oxide exposure. For example, changes in optical properties, such as a change in optical polarization; or changes in electrical properties, such as those found using nematic structures used in liquid crystal display devices may be used for quantitatively measuring ethylene oxide exposure.

The structure depicted in FIG. 2 is similar to that in FIG. 1 except that the liquid crystal coating 28 is applied directly to the surface of the absorbant layer 30. The close proximity of the liquid crystal coating 28 and the absorbant layer 30 enhances the sensitivity of the indicator to ethylene oxide.

The embodiment of FIG. 3 is similar to the examples of FIGS. 1 and 2 except that the ethylene oxide absorbing agent is incorporated with the liquid crystal coating formulation as a composite 54. This structure may be particularly useful when the liquid crystal composition has been microencapsulated and the absorbant is activated charcoal. This structure may be especially sensitive to ethylene oxide.

FIGS. 4 and 5 illustrate clip-on badges of the type which may be worn by personnel, for continuously indicating ethylene oxide exposure. In the badge 60 FIG. 4, the control area 64 of the indicator appears as a "bull's eye" and the test area 66 encircles the control area 64. Both "areas" are carried in a holder 70 provided with a clip 72. In the badge 80 of FIG. 5, the control area 84 and the test area 86 form two zones of a disc mounted in a holder 90 which carries a clip 92. The overlapping or adjacent positioning of the control 84 and test 86 areas has the effect of accentuating any color difference between the control and test areas, rendering the difference more discernible.

To be used as a dosimeter, the indicator device of the invention is removed from an airtight storage package (not shown) such as an aluminum foil pouch. It is then attached near one's breathing zone (e.g., lapel, or shirt pocket). As the wearer moves in and out of work areas, which may have different concentrations of ethylene oxide in the environment, the absorbant of the indicator extracts ethylene oxide from the air. As the concentration of ethylene oxide in the absorbant increases, the liquid crystal coating in the test area exhibits a color change. A comparison between the color of the control area and the test area provides an immediate visual indication of the wearer's exposure to ethylene oxide. For example, if one has been exposed to a short term high concentration of ethylene oxide, a color change will be observed in the control area. This color change will provide a quantitative indication of the ethylene oxide concentration in the environment. The color of the *control area* will revert to its normal pre-exposed color when the indicator is removed from the environment containing high ethylene oxide levels. But, since the absorption of ethylene oxide by the absorbant is cumulative, even short term exposures to high ethylene oxide concentrations would cause permanent changes in the color of the *test area*.

While the present invention has been described and characterized with reference to several preferred embodiments, variations in and additions to the specific structures depicted are contemplated. For example, it is anticipated that, depending upon controlling environmental parameters and upon the nature of the gases and other system contaminants to be assayed or measured, the incorporation of attenuating media into the dosimeters of the invention may constitute a desirable requirement. Suitable attenuators would include sintered metals or fine metallic screens, woven fabrics, sintered glass and other mineral materials, as well as porous sheet material including polymeric fibers, and batting including non-woven materials. Such attenuating agents would serve to ensure that the amount of the gas at hand for analysis will be a direct function of the concentration of that gas in the system being investigated, and independent of gas movement velocity and other physical parameters.

It is contemplated that the indicator of the invention would be worn by each employee during the work period. At the end of a given work period, the color difference between the control and test areas of the indicator would be noted, and the worker's exposure to ethylene oxide would be determined and recorded. It is also apparent that the indicator, rather than or in addition to being worn by an individual, may be placed in a work environment to monitor areas which are likely to contain ethylene oxide.

This disclosure has described an indicator device for personal use and for area monitoring of ethylene oxide. A quantitative measurement of the exposure to ethylene oxide is immediately evidenced by any perceived color difference between a liquid crystal coating in a control and in a test area of the device. The technology taught in the present invention may be applied to the monitoring of other gases or vapors such as nitrous oxide, anaesthetic vapors, and other environmental contaminants.

What is claimed is:

1. A dosimeter for providing a contemporaneous, on-going visual indication of the total cumulative concentration of ethylene oxide to which a wearer of said dosimeter has been exposed, said dosimeter comprising,
   first sensor means responsive to ethylene oxide for enabling a continuous determination of the current concentration of ethylene oxide in an ambient environment,
   said first sensor means constituting a control reference area,
   gas-absorbing means for extracting, absorbing, retaining and cumulatively integrating ethylene oxide gas concentration present in an ambient environment,
   second sensor means in gas-sensing communication with said gas-absorbing means for reacting with ethylene oxide gas absorbed in and concentrated by said gas-absorbing means to permit a cumulative, quantitiative determination of total gas absorbed by said gas-absorbing means, and to indicate a wearer's total exposure to ethylene oxide over a time-weighted average,
   said first and said second sensor means comprising liquid crystal compositions which exhibit color changes when exposed to ethylene oxide gas and siad first sensor means and said second sensor means being responsive to undergo color changes upon exposure to ethylene oxide whereby temperature effects between the two sensor means are cancelled, and wherein differences in color between said first sensor means and said second sensor means provide a quantitative indication of a concentration of ethylene oxide to which said dosimeter has been exposed.

2. The structure as set forth in claim 1 wherein said gas-absorbing means is selected from the group consisting of activated charcoal, silica gel, alumina, and mixtures thereof.

3. The structure as set forth in claim 1 wherein said liquid crystal compositions include cholesteric esters in combination with a binder selected from the group consisting of gelatin, polyvinyl alcohol, cellulose polymers, latex resins, acrylic resins, and mixtures thereof.

4. The structure as set forth in claim 1 wherein said liquid crystal compositions include cholesteric esters present as an encapsulated phase.

5. The structure as set forth in claim 1 wherein said first and said second sensor means comprise mixtures of cholesteric liquid crystal compositions.

6. The structure as set forth in claim 1 and further comprising attenuating means for controlling diffusion of gas to said second sensor means, said attenuating means being interposed physically between ambient atmosphere and said liquid crystal compositions of said second sensor means.

7. A device for indicating simultaneously and concurrently the concentration of ethylene oxide present in an ambient atmosphere and the total accumulated amount of ethylene oxide to which a wearer of the device has been exposed, said device comprising an assembly including:
   a test portion and a control portion;
   said test portion comprising substrate means for supporting a liquid crystal coating composition thereon,
   a first liquid crystal composition deposited as a coating on said substrate means,
   gas-absorbing means for extracting, absorbing, and for retaining of ethylene oxide derived from an ambient environment and for building-up ethylene oxide concentrations in said gas absorbing means,
   said gas absorbing means being adhered to said substrate means and being in gas-diffusion communication with said first liquid crystal compositions,
   whereby ethylene oxide accumulated in said gas-absorbing means acts upon said liquid crystal composition to effect therein a color change correlated with an accumulated, total exposure of said device to ethylene oxide; said control portion comprising an ethylene oxide impermeable barrier film,
   a second liquid crystal composition coating a top surface of said barrier film, and
   means bonding said barrier film of said control portion to overlie said test portion;
   said second liquid crystal composition being responsive to ethylene oxide to undergo color changes and to assume a color correlated with existing and with changing concentrations of ethylene oxide present in an ambient environment.

8. The structure as set forth in claim 7 wherein said first liquid crystal composition and said second liquid crystal composition each comprises a mixture of cholesteric liquid crystals and wherein said mixture is the same for each liquid crystal composition.

9. The structure as set forth in claim 7 wherein said assembly comprises a test portion and a control portion which 10. The structure as set forth in claim 7 wherein said assembly comprises a test portion and a control portion which define laterally adjacent and contiguous areas. define overlapping areas.

11. The structure as set forth in claim 7 and further comprising attenuating means for controlling diffusion of ethylene oxide gas to said first liquid crystal composition, said attenuating means being interposed physically between ambient atmosphere and said first liquid crystal composition.

* * * * *